US008666473B2

(12) United States Patent
Gleich (10) Patent No.: US 8,666,473 B2
(45) Date of Patent: Mar. 4, 2014

(54) ARRANGEMENT AND METHOD FOR INFLUENCING AND/OR DETECTING MAGNETIC PARTICLES AND FOR MAGNETIC RESONANCE IMAGING

(75) Inventor: Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 27 days.

(21) Appl. No.: 13/266,507

(22) PCT Filed: Apr. 23, 2010

(86) PCT No.: PCT/IB2010/051790
§ 371 (c)(1),
(2), (4) Date: Jan. 16, 2012

(87) PCT Pub. No.: WO2010/125510
PCT Pub. Date: Nov. 4, 2010

(65) Prior Publication Data
US 2012/0119739 A1      May 17, 2012

(30) Foreign Application Priority Data

Apr. 30, 2009  (EP) .................................. 09159257

(51) Int. Cl.
*A61B 5/05*      (2006.01)
*G01R 33/12*     (2006.01)
*G01N 27/72*     (2006.01)
(52) U.S. Cl.
USPC ......................................... 600/409; 328/228

(58) Field of Classification Search
USPC .......... 600/407, 420, 409, 422–425; 328/204, 328/228, 307, 309, 318; 607/105; 73/53.01; 702/57
See application file for complete search history.

(56) References Cited

U.S. PATENT DOCUMENTS

| 4,680,551 | A | * | 7/1987 | O'Donnell et al. ............ 324/320 |
| 2003/0085703 | A1 | * | 5/2003 | Gleich ............................. 324/309 |
| 2005/0083057 | A1 | * | 4/2005 | Schulz et al. .................. 324/318 |
| 2009/0115415 | A1 | * | 5/2009 | Weaver et al. ................. 324/309 |

FOREIGN PATENT DOCUMENTS

| DE | 10151778 A1 | 10/2011 |
| EP | 1304542 A3 | 4/2003 |
| WO | 2006033047 A2 | 3/2006 |
| WO | 2009008956 A2 | 1/2009 |

OTHER PUBLICATIONS

Gleich et al.: "Tomographic Imaging Using the Nonlinear Response of Magnetic Particles" Nature Publishing Group, Jun. 2005, pp. 1214-1217.
A. Macovski et al.: "Novel Approaches to Low-Cost MRI" Magnetic Resonance in Medicine, XP000385356, Aug. 30, 1993, No. 2, Academic Press, Duluth, MN, US, vol. 30, No. 2, Aug. 1, 1993, pp. 221-230, XP000385356 ISSN: 0740-3194.

* cited by examiner

*Primary Examiner* — Long V. Le
*Assistant Examiner* — Lawrence Laryea (57) ABSTRACT

Magnetic particle imaging allows the imaging of fast tracer dynamics, but there is no native tissue contrast. A combination with MRI solves this issue. However, coil geometries in MPI and MRI differ significantly, making direct use impractical. According to one aspect of the present invention it is proposed to use pre-polarized MRI to overcome these difficulties. Further, methods and arrangements are proposed to achieve MRI imaging with minimal additional hardware.

17 Claims, 5 Drawing Sheets

ARRANGEMENT AND METHOD FOR INFLUENCING AND/OR DETECTING MAGNETIC PARTICLES AND FOR MAGNETIC RESONANCE IMAGING

FIELD OF THE INVENTION

The present invention relates to an arrangement and a method for influencing and/or detecting magnetic particles in a region of action and for magnetic resonance imaging of an examination object in said region of action. Further, the present invention relates to a computer program for implementing said method on a computer and to control such an arrangement.

BACKGROUND OF THE INVENTION

An arrangement for influencing and/or detecting magnetic particles in a region of action is known from German patent application DE 101 51 778 A1. In the arrangement described in that publication, first of all a magnetic selection field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e.g. human bodies—in a non-destructive manner and without causing any damage and with a high spatial resolution, both close to the surface and remote from the surface of the examination object.

A similar arrangement and method is known from Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication takes advantage of the non-linear magnetization curve of small magnetic particles.

Arrangements and methods for magnetic resonance imaging (MRI) are widely known in the art. MR imaging has become one of the main imaging modalities, in particular in the medical field, and the details of the general layout of and MR system and the standard methods for MR imaging are described in many publications and standard books.

A combination of MPI and MRI would be very useful for a clinical acceptance of MPI. An MRI scan could be useful for planning the MPI examination or for identifying tissue parameters that are not accessible my MPI alone. For some patients, the scanner may be used as a pure MRI scanner if no MPI examination is scheduled.

SUMMARY OF THE INVENTION

It is an object of the present invention to provide an arrangement and a method for influencing and/or detecting magnetic particles in a region of action and for magnetic resonance imaging of an examination object in said region of action, i.e. which allows to use the same hardware selectively for MPI data acquisition or MRI data acquisition or, in a combined mode, for data acquisition for both MPI and MRI.

In a first aspect of the present invention an arrangement for influencing and/or detecting magnetic particles in a region of action and for magnetic resonance imaging of an examination object in said region of action is presented comprising:

a set of coils for generating
  i) a stationary magnetic gradient field having a pattern in space of its magnetic field strength such that a first sub-zone having a low magnetic field strength and a second sub-zone having a higher magnetic field strength are formed in the region of action,
  ii) a temporally changing homogeneous magnetic field for changing the position in space of the region of action and for changing the position in space of the two sub-zones in the region of action so that the magnetization of the magnetic material changes locally,
  iii) a substantially homogeneous main magnetic field in a selected and changeable direction, and
  iv) a magnetic gradient field in at least two selected and changeable directions, an excitation means for exciting magnetic spins in the region of action to precess,
a receiving means for selectively acquiring magnetic resonance signals and detection signals depending on the magnetization in the region of action, which magnetization is influenced by the change in the position in space of the first and second sub-zone,
signal generation means for generating and providing field generation signals to said set of coils,
control means for controlling said signal generation means, and
processing means for processing said detection signals and said magnetic resonance signals.

For a combined arrangement (usable for MPI and MPI data acquisitions), as many MPI components as possible should be used for MRI. However, although MPI selection field coils can produce quite strong (0.4 . . . 0.6 T) homogeneous fields, if a reverse current in one of the coil elements is applied compared to one or more of the other coil elements, the homogeneity is not good enough for an MRI operation. MPI usually generates RF fields useful for MRI only below 100 kHz, limiting the main field strength to a few mT. The receive coils typically operate below 2 MHz which limits the main field strength to 50 mT.

The present invention is thus based on the idea to use the MPI system as pre-polarized MRI system. This means that the protons are polarized by applying the strong homogeneous field for some time, e.g. several 100 ms. The RF pulses, spatial encoding and read-out of the MR signals is then done at a lower field strength.

The arrangement proposed according to the present invention particularly comprises a set of coils which is able to generate various (homogenous and gradient) magnet fields, in particular a substantially homogeneous main magnetic field in a selected and changeable direction as well as a magnetic gradient field in at least two, preferably three, selected and changeable directions. The substantially homogeneous main magnetic field and the magnetic gradient field are generally almost stationary, but slowly varying (i.e. slowly compared to the magnetic drive field as explained below). These magnetic fields can have frequency components up to approximately 1 kHz.

Preferably, the set of coils should be able to generate the field free point (FFP), i.e. first sub-zone having a low magnetic field strength, having a value of 40 T/sec<dB/dT>0.2 T/sec and having a field strength of at least 100 mT. Further, it shall be able to generate a fast oscillating field homogenous (also called drive field) having a value of dB/dT>100 T/sec, preferably >1000 T/sec.

According to a preferred embodiment said set of coils comprises a number of subsets, in particular three subsets, wherein a first subset of coils is provided for generating said magnetic gradient field, a second subset of coils is provided for generating said temporally changing homogenous magnetic field for changing the position in space of the region of action, and a third subset of coils is provided for generating said temporally changing homogenous magnetic field for changing the position in space of the two sub-zones in the region of action so that the magnetization of the magnetic material changes locally. This embodiment provides sufficient flexibility to generate the desired magnetic fields depending on the mode of application. For this purpose, each subset is individually addressable and controllable, e.g. for each subset a separate generation means is separately provided for generating and providing field generation signals to said subsets of coils.

According to a further preferred embodiment the first subset of coils comprises selection field coils for generating a magnetic selection field as said magnetic gradient field, said second subset of coils comprises focus field coils for generating a magnetic focus field as a temporally changing homogenous field for changing the position in space of the region of action, and said third subset of coils comprises drive field coils for generating a magnetic drive field as said temporally changing homogenous magnetic fields for changing the position in space of the two sub-zones in the region of action so that the magnetization of the magnetic material changes locally. In other words, the coils generally provided in an MPI system are advantageously used for generating the required magnetic fields in the MRI mode to acquire magnetic resonance signals. Thus, generally no additional hardware is required in the arrangement that can be used in both modes.

Preferably said substantially homogenous main magnetic field in a selected and changeable direction is generated by said first and/or second subset of coils and said magnetic gradient field in at least two selected and changeable directions is generated by said second subset of coils. This ensures an efficient use of the available subsets of coils without the need to add further coils for specific use in the MRI mode.

In an advantageous embodiment said first subset of coils (e.g. the selection field coils) comprises a number of at least two, in particular a pair, of first coil elements located on opposite sides of the region of action, each first coil element being provided with a separate first field generation signal from said signal generation means. In other words, each of said first coil elements is separately controllable and providable with a first field generation signal, depending on which kind of magnetic field shall be generated therewith. For instance, in the MPI mode said first subset of coils is controlled such that a magnetic gradient field is generated having a pattern in space such that a first sub-zone having a low magnetic field strength and a second sub-zone having a higher magnetic field strength are formed in the region of action for which purpose, in case of oppositely arranged two coil elements, these coil elements are provided with oppositely oriented currents. In the MRI mode, however, both coil elements are provided with identically oriented currents to generate said substantially homogenous main magnetic field.

The second subset of coils preferably comprises a number of at least six, in particular three pairs, of second coil elements located on opposite sides of the region of action, each coil element being provided with a separate second field generation signal from said signal generation means. The coils of said second subset, which are preferably the focus field coils of the MPI system, can be used for generating the main magnetic field as well as the gradient fields in the MRI mode, depending on how they are provided with second field generation signals. In particular, if the coil elements of a pair of oppositely arranged coil elements are provided with oppositely oriented currents, a gradient field will be generated.

As mentioned above the arrangement according to the present invention can be used in various modes, in particular a magnetic particle imaging mode and a magnetic resonance imaging mode as well as a combined mode, in which particularly some waiting time required in the magnetic resonance imaging mode is used for obtaining magnetic particle imaging signals. The control means is accordingly adapted to switch between the various modes and to control the signal generation means accordingly so that the coils of the set of coils generate the required magnetic fields for the respective mode.

To provide a sufficient homogeneity for the main magnetic field in the MRI mode shimming coils are provided in an embodiment for generating a stationary and substantially homogenous main magnetic field in MRI mode. These shimming coils can be operated alone or in addition to the first and/or second subset of coils for generating the homogenous main field in the MRI mode, since the homogeneity provided by the first and/or second subset of coils might be too low for certain applications.

For exciting the magnetic spins in the region of action to precess in the MRI mode various options exist. According to one embodiment the excitation means comprises an RF transmit coil and/or an RF signal generator coupled to said receiving means, in particular a receiving coil for generating RF transmit signals in an MRI mode. This means particularly that an RF signal generator is additionally provided which either uses the available receiving coil as a transmit coil or which use an additionally provided RF transmit coil for generating RF pulse signals for exciting the magnetic spins in the region of action to precess. This kind of excitation in generally known in the art of MRI.

According to another embodiment the control means is adapted to controlling the signal generation means to generate and provide field generation signals to said set of coils to generate a magnetic field having bent magnetic field lines. This provides a further degree of freedom to generate a very inhomogenous main magnetic field in the MRI mode which is, for instance, usable for sensitivity encoding as is generally known in the art of MR.

According to still another embodiment the control means is adapted for controlling said signal generation means to generate and provide field generation signals to said set of coils to subsequently
  generate a strong magnetic gradient field,
  reduce the gradient of said magnetic gradient field and add a substantially homogeneous magnetic field, and
  reduce the field strength of said magnetic gradient field,
and that magnetic resonance signals are then acquired. Also in this way the magnetic spins in the region of action can be effectively excited without the need for additional excitation means.

According to another alternative embodiment the third subset of coils is adapted for generating RF transmit signals in magnetic resonance imaging mode. The third subset of coils, in particular drive field coils, can thus be used according to the present invention for generating the $B_1$ field in a magnetic resonance imaging mode, in particular if the main magnetic field ($B_0$) is made sufficiently small (e.g. 2.4 mT for 100 kHz). Further, they can be used when the main magnetic field is reduced to zero and then increased again with a different magnetization direction as explained above. Between these ways of use there is a smooth transition. If the field intensity of the drive field coil reaches the field intensity of the $B_0$ field, the spins can be excited even if the resonance condition (i.e. drive field frequency equals the Larmor frequency of the $B_0$ field) is not fulfilled since the $B_0$ field changes continuously.

According to still another alternative embodiment the excitation means are adapted for generating an RF flip in magnetic resonance imaging mode by generating and providing a current for application to a patient's body. Hence, the patient can be provided with electrodes to which an appropriate voltage is applied. The current through the patient generates a magnetic field which causes the desired MR excitation. Typically, the current must not be too large, typically some µA up to some mA, and should be applied to the patient's extremities only with large area electrodes. The advantage of this embodiment is that an AC current having a frequency of above 10 kHz can be used with the arrangement according to the present invention which does not well excite the nerves and which enables the use of an increased current (up to 1 A), so that the SNR in such an arrangement can be significantly improved.

In a combined MPI/MRI mode the control means is adapted for controlling said signal generation means to generate and provide field generation signals to said set of coils for pre-polarizing protons at portions of the region of action for subsequent acquisition of magnetic resonance signal from said portions, while detection signals are acquired from other portions of said region of action. In this way some waiting time that is required for pre-polarizing magnetic particles in a certain area can be used to acquire magnetic particle imaging signals in another area.

According to another aspect of the present invention an arrangement for influencing and/or detecting magnetic particles in a region of action and for magnetic resonance imaging of an examination object in said region of action is presented, said arrangement comprising:

a set of coils for generating magnetic fields in said region of action, an excitation means for exciting magnetic spins in the region of action to precess, a receiving means for selectively acquiring magnetic resonance signals and detection signals depending on the magnetization in the region of action, which magnetization is influenced by the change in the position in space of the first and second sub-zone, signal generation means for generating and providing field generation signals to said set of coils, control means for controlling said signal generation means, and processing means for processing said detection signals and said magnetic resonance signals, wherein said control means is adapted for controlling said signal generation means to generate and provide field generation signals to said set of coils to subsequently generate in the region of action a magnetic gradient field, a first substantially homogenous magnetic field in a first magnetization direction, after reducing the field intensity of the first substantially homogenous magnetic field, in particular to substantially zero, a substantially homogenous magnetic field in a second magnetization direction which is substantially different from the first magnetization direction.

This provides another option to excite the magnetic spins in the region of action to precess without the need of any additional hardware elements as explained above in other embodiments.

According to a further aspect of the present invention a method for influencing and/or detecting magnetic particles in a region of action and for magnetic resonance imaging of an examination object in said region of action is presented, which method comprises the steps of subsequently generating in the region of action a magnetic gradient field, a first substantially homogenous magnetic field in a first magnetization direction, after reducing the field intensity of the first substantially homogenous magnetic field, in particular to substantially zero, a substantially homogenous magnetic field in a second magnetization direction which is substantially different from the first magnetization direction.

Finally, the present invention is directed to a computer program comprising program code means for causing a computer to control an arrangement according to the present invention to carry out the steps of the method according to the present invention when said computer program is carried out on the computer.

It shall be understood that all claimed methods and arrangements as well as the claimed computer program may have similar and/or identical preferred embodiments as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in details with reference to FIGS. 1 to 4.

Figure 1:
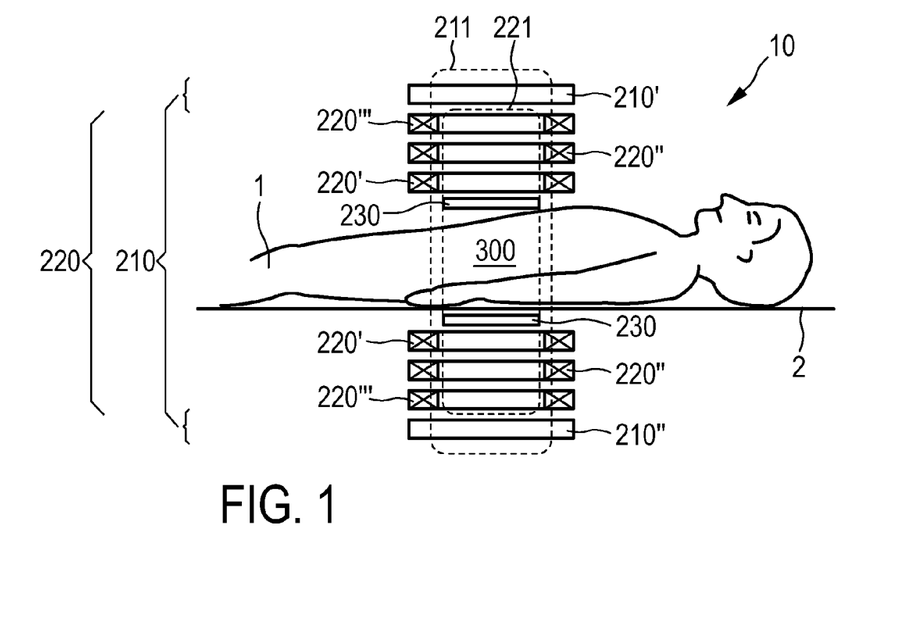
FIG. 1 shows a schematic view of the principle layout of a magnetic particle imaging (MPI) arrangement.

FIG. 1 shows an arbitrary object to be examined by means of a MPI arrangement 10. The reference numeral 1 in FIG. 1 denotes an object, in this case a human or animal patient, who is arranged on a patient table 2, only part of the top of which is shown. Prior to the application of the imaging method, magnetic particles 100 (not shown in FIG. 1) are arranged in a region of action 300 of the inventive arrangement 10. Especially prior to a therapeutic and/or diagnostic treatment of, for example, a tumor, the magnetic particles 100 are positioned in the region of action 300, e.g. by means of a liquid (not shown) comprising the magnetic particles 100 which is injected into the body of the patient 1.

Figure 2:
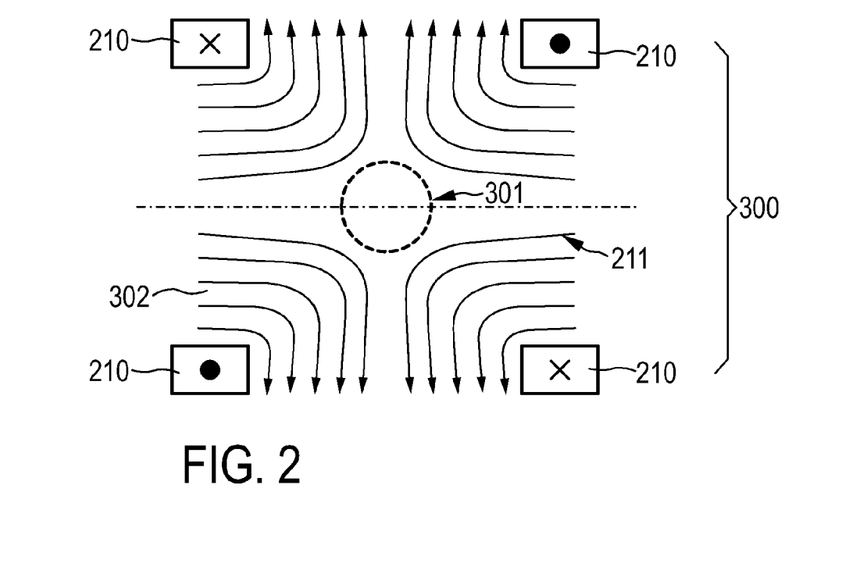
FIG. 2 shows an example of the field line pattern produced by an arrangement as shown in FIG. 1.

As an example of an arrangement of coils is shown in FIG. 2 comprising a plurality of coils forming a selection means 210 whose range defines the region of action 300 which is also called the region of treatment 300. For example, the selection means 210 is arranged above and below the patient 1 or above and below the table top. For example, the selection means 210 comprise a first pair of coils 210', 210", each comprising two identically constructed windings 210' and 210" which are arranged coaxially above and below the patient 1 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
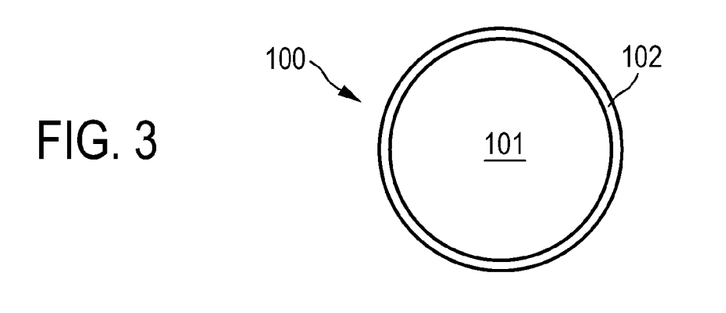
FIG. 3 shows an enlarged view of a magnetic particle present in the region of action.

FIG. 3 shows an example of a magnetic particle 100 of the kind used together with an arrangement 10 as shown above, but also according to the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to $160 \cdot 10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220''' which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220''' are provided in order to generate components of the magnetic drive field 221 which extend in a different direction in space, e.g. horizontally in the longitudinal direction of the region of action 300 (or the patient 1) and in a direction perpendicular thereto. If third and fourth coil pairs 220", 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220''' are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

The arrangement 10 further comprises receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
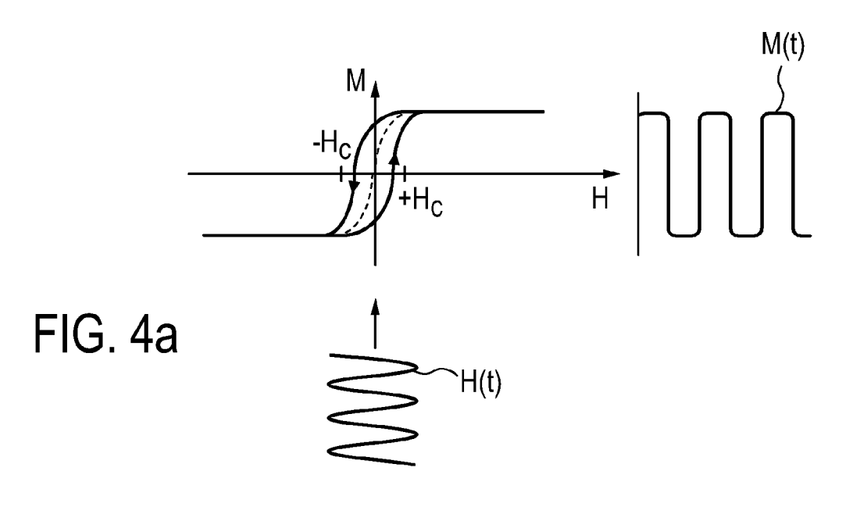
FIGS. 4a and 4b show the magnetization characteristics of such particles.
Figure 4B:
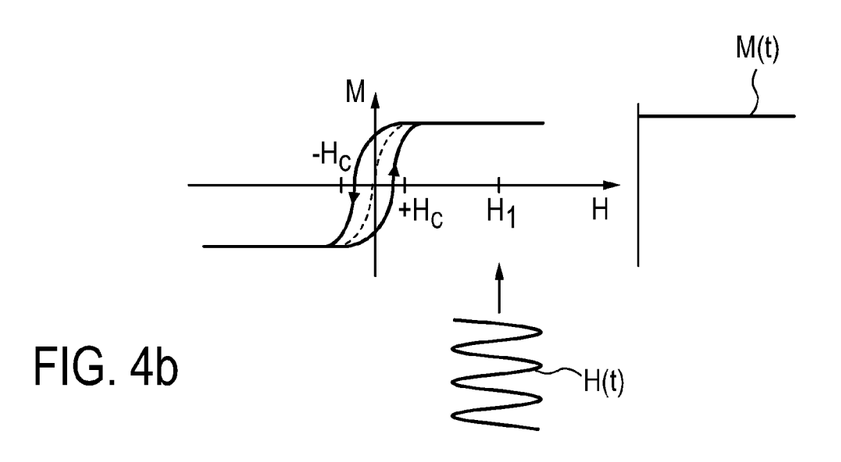

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
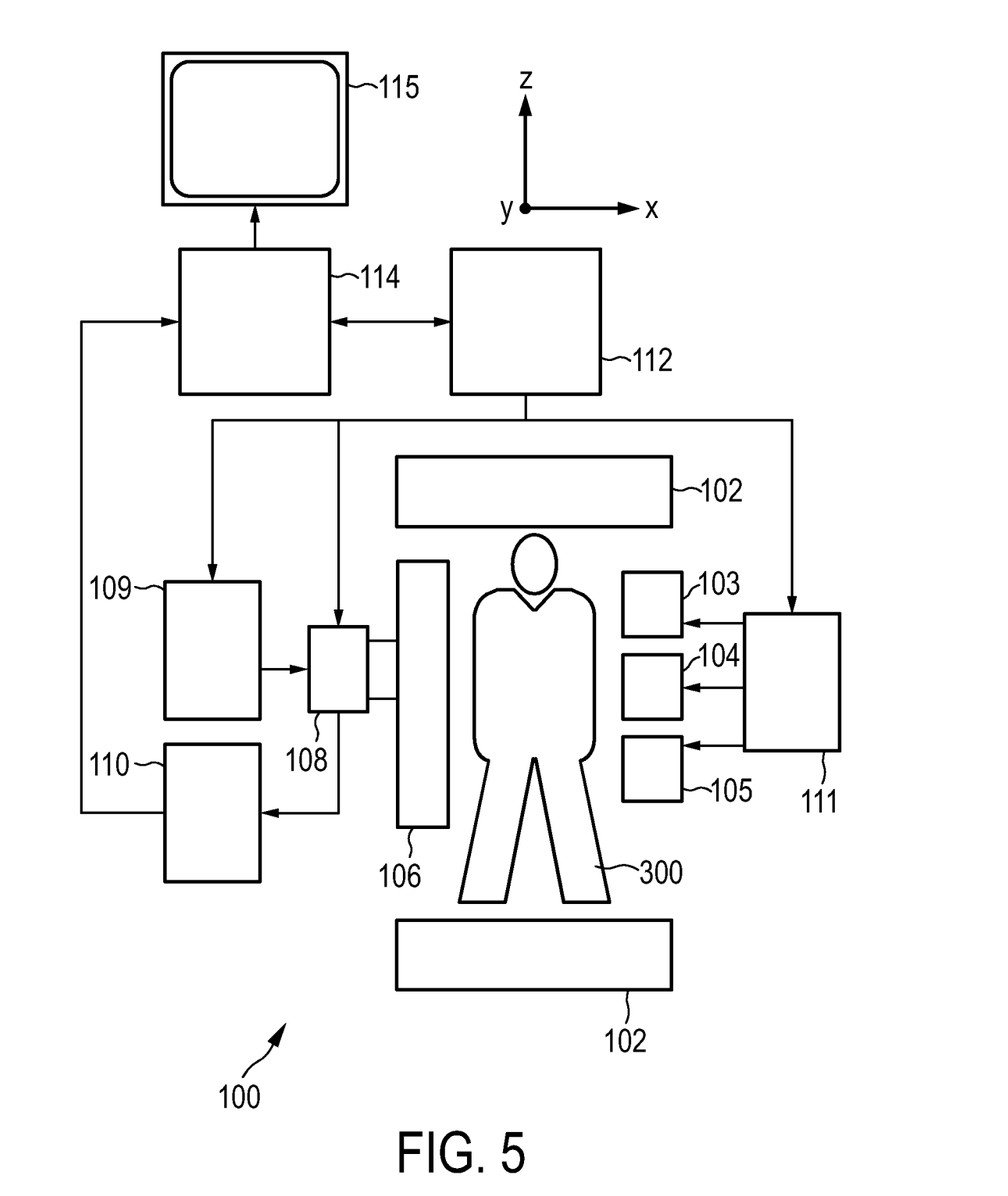
FIG. 5 shows a block diagram of a convention MR apparatus.

In FIG. 5 the general layout of an MR imaging device, as for instance described in WO 2006/033047 A, is illustrated as a block diagram. The apparatus 100 comprises a set of main magnetic coils 102 for generating a stationary and homogeneous main magnetic field and three sets of gradient coils 103, 104 and 105 for superimposing additional magnetic fields with controllable strength and having a gradient in a selected direction. Conventionally, the direction of the main magnetic field is labelled the z-direction, the two directions perpendicular thereto the x- and y-directions. The gradient coils 103, 104, and 105 are energized via a power supply 111. The apparatus 100 further comprises an RF transmit antenna 106, for example a conventional quadrature body coil, for emitting RF pulses to a body 107. Being a quadrature coil, the antenna 106 has two resonance modes that are conventionally excited by RF signals having the same amplitudes and a phase difference of 90°. In accordance with the invention, the antenna 106 is connected to a receive/transmit unit 108 for controlling the phases and amplitudes of the two different resonance modes of the antenna 6. The receive/transmit unit 108 is further coupled to a modulator 109 for generating and modulating the RF pulses.

As shown in FIG. 5, the RF transmit antenna and the receiving antenna are physically the same antenna 106. Therefore, the transmit/receive unit 109 is arranged to separate the received signals from the RF pulses to be emitted. The received MR signals are input to a demodulator 110. The transmit/receive unit 108, the modulator 109, and the power supply 111 for the gradient coils 103, 104 and 105 are controlled by a control system 112. Control system 112 controls the phases and amplitudes of the RF signals fed to the antenna 106 on the basis of the aspect ratio of the body 300. The control system 112 is usually a microcomputer with a memory and a program control. The demodulator 110 is coupled to a data processing unit 114, for example a computer, for transformation of the received echo signals (also called magnetic resonance signals) into an image that can be made visible, for example, on a visual display unit 115.

Figure 6:
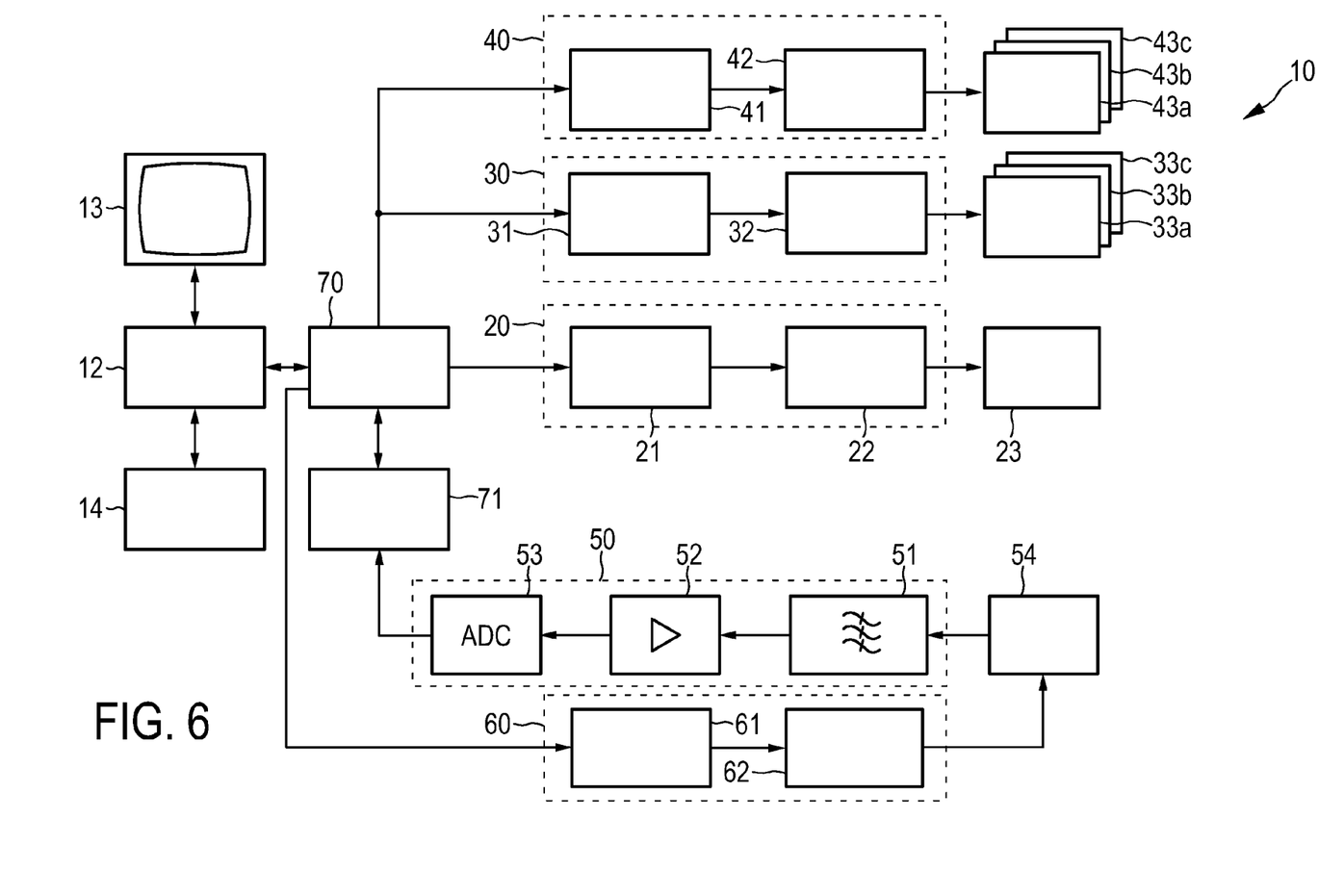
FIG. 6 shows a block diagram of an embodiment of the arrangement according to the present invention.

FIG. 6 shows a block diagram of an embodiment of the apparatus 10 according to the present invention. The general principles of magnetic particle imaging and of magnetic resonance imaging explained above are valid and applicable here as well, unless otherwise specified.

The embodiment of the apparatus 10 shown in FIG. 6 comprises a set of various coils for generating the desired magnetic fields, desired on the mode of operation of the apparatus 10. First, the coils and their functions in a MPI mode shall be explained.

For generating the magnetic selection field explained above selection means are provided comprising a subset of selection field (SF) coils 23, preferably comprising a pair of coil elements, for generating said magnetic gradient field.

The selection means further comprises a selection field signal generator unit 20. Preferably, a separate generator subunit is provided for each coil element of the subset 23 of selection field coils. Said selection field signal generator unit 20 comprises a controllable selection field current source 21 (generally including an amplifier) and a filter unit 22 which provide the respective section field coil element with the selection field current to individually set the gradient strength of the selection field in the desired direction. Preferably, a DC current is provided. If the selection field coil elements are arranged as opposed coils, e.g. on opposite sides of the region of action, the selection field currents of opposed coils are preferably oppositely oriented.

The selection field signal generator unit 20 is controlled by a control unit 70, which preferably controls the selection field current generation such that the sum of the field strength and the sum of the gradient strength of all spatial fractions of the selection field is maintained at a predefined level.

For generation of a magnetic focus field the apparatus 10 further comprises focus means comprising a subset of focus field (FF) coils 33a, 33b, 33c, preferably comprising three pairs 33a, 33b, 33c of oppositely arranged focus field coil elements. Said magnetic focus field is generally used for changing the position in space of the region of action as is generally known in the art of MPI. The apparatus 10 further comprises a focus field signal generator unit 30 comprising a focus field current source 31 (preferably comprising a current amplifier) and a filter unit 32 for providing a focus field current to the respective coil of said subset of coils 33a, 33b, 33c which shall be used for generating the magnetic focus field. The focus field current source 31 is also controlled by the control unit 70.

For generation of the magnetic drive field the apparatus 10 further comprises drive means comprising a subset of drive field (DF) coils 43a, 43b, 43c, preferably comprising three pairs 43a, 43b, 43c of oppositely arranged drive field coil elements. Said magnetic drive field is generally used as said temporally changing homogeneous magnetic field for changing the position in space of the two sub-zones in the region of action so that the magnetization of the magnetic material changes locally. The apparatus 10 further comprises a drive field signal generator unit 40, preferably a separate drive field signal generation unit for each coil element of said set subset of drive field coils 43a, 43b, 43c. Said drive field signal generator unit 40 comprises a drive field current source 41 (preferably including a current amplifier) and a filter unit 42 for providing a drive field current to the respective drive field coil. The drive field current source 41 is adapted for generating an AC current and is also controlled by the control unit 70.

For signal detection receiving means 54, in particular a receiving coil, and a signal receiving unit 50, which receives signals detected by said receiving means 54, are provided. Said signal receiving unit 50 comprises a filter unit 51 for filtering the received detection signals. The aim of this filtering is to separate measured values, which are caused by the magnetization in the examination area which is influenced by the change in position of the two part-regions (301, 302), from other, interfering signals. To this end, the filter unit 51 may be designed for example such that signals which have temporal frequencies that are smaller than the temporal frequencies with which the receiving coil 54 is operated, or smaller than twice these temporal frequencies, do not pass the filter unit 51. The signals are then transmitted via an amplifier unit 52 to an analog/digital converter 53 (ADC). The digitalized signals produced by the analog/digital converter 53 are fed to an image processing unit (also called reconstruction means) 71, which reconstructs the spatial distribution of the magnetic particles from these signals and the respective position which the first part-region 301 of the first magnetic field in the examination area assumed during receipt of the respective signal and which the image processing unit 71 obtains from the control unit 70. The reconstructed spatial distribution of the magnetic particles is finally transmitted via the control means 70 to a computer 12, which displays it on a monitor 13. Thus, an image can be displayed showing the distribution of magnetic particles in the examination area.

Further, an input unit 14 is provided, for example a keyboard. A user is therefore able to set the desired direction of the highest resolution and in turn receives the respective image of the region of action on the monitor 13. If the critical direction, in which the highest resolution is needed, deviates from the direction set first by the user, the user can still vary the direction manually in order to produce a further image with an improved imaging resolution. This resolution improvement process can also be operated automatically by the control unit 70 and the computer 12. The control unit 70 in this embodiment sets the gradient field in a first direction which is automatically estimated or set as start value by the user. The direction of the gradient field is then varied stepwise until the resolution of the thereby received images, which are compared by the computer 12, is maximal, respectively not improved anymore. The most critical direction can therefore be found respectively adapted automatically in order to receive the highest possible resolution.

According to the present invention the arrangement as illustrated in FIG. 5, which is generally designed for magnetic particle imaging is adapted such that it is also usable for magnetic resonance imaging. In particular, the set of coils provided in the MPI arrangement are controlled and provided with field generating currents such that the magnetic fields required for MRI can be generated as will be explained below.

The set of coils is particularly able to generate a substantially homogeneous main magnetic field in a selected and changeable direction, for which purpose preferably the selection field coils 23 and/or one or more of the focus field coils 33a, 33b, 33c are used. The set of coils is further able to generate a magnetic gradient field in at least two, preferably three orthogonal, selected and changeable directions, for which purpose preferably the focus field coils 33a, 33b, 33c are used. Further, an excitation means is provided for exciting magnetic spins in the region of action to precess, for which various embodiments exist as will be explained in detail below.

It shall be noted that the subsets of coils preferably comprise pairs of oppositely arrange coil elements. But it is also possible that instead of pairs more than two coil elements for generating the desired magnetic fields, e.g. three or four coil elements, are used. Further, according to an embodiment of the present invention all coils elements of the selection field coils 23 and of the focus field coils 33a, 33b, 33c are provided with a separate generator sub-unit (which may be part of a common generator unit) to individually control each coil element for generation of the desired magnetic field. The drive field coils 43a, 43b, 43c can have integrated receive coils and the focus field coils 33a, 33b, 33c can also serve as the selection field coils 23.

The control unit 70 is adapted for controlling the various generator unit to work in a MPI mode, a MRI mode or in a combined MPI/MRI mode, i.e. to switch between said mode (in particular in response to a user command) and to generate the respective control signals for the respective coils.

According to an aspect of the present invention it is proposed to use the MPI system as pre-polarized MRI system. This means that the protons are polarized by applying the strong homogeneous field for several 100 ms. The RF pulses, spatial encoding and read-out is done at a lower field strength. Such a pre-polarized MRI system is described by Macovski A, Conolly S, "Novel approaches to low-cost MRI", Magn. Reson. Med. 1993 Aug. 30, (2):221-30. In Prepolarized MRI (PMRI) with pulsed electromagnets, the main magnetic field cycles between a high field (Bp) to polarize the sample and a homogeneous, low field (B0) for data acquisition. This architecture combines the higher SNR of the polarizing field with the imaging benefits of the lower field. However, PMRI can only achieve high SNR efficiency for volumetric imaging with 3D rapid imaging techniques, such as rapid acquisition with relaxation enhancement (RARE) (FSE, TSE), because slice-interleaved acquisition and longitudinal magnetization storage are both inefficient in PMRI.

Figure 7:
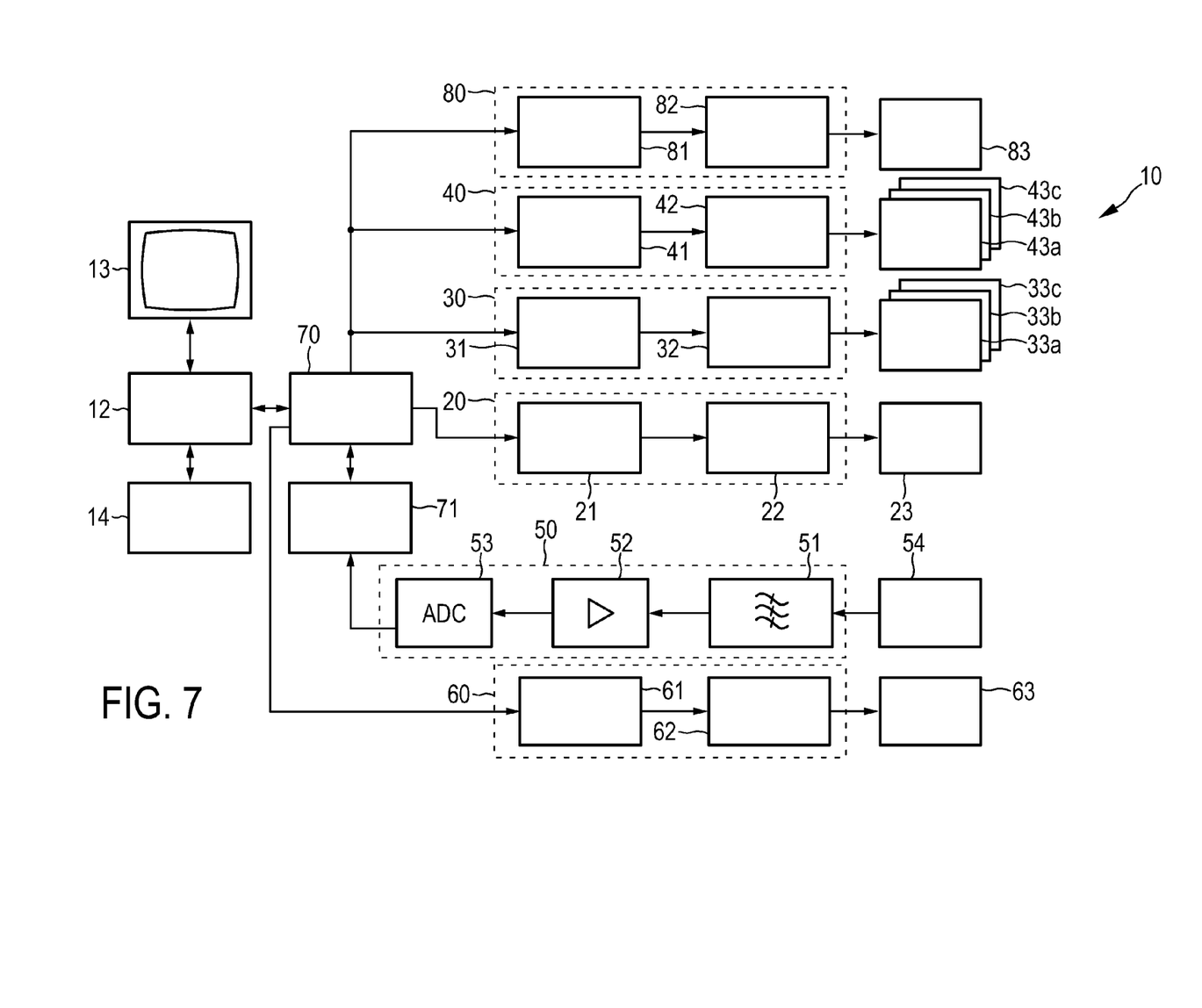
FIG. 7 shows a block diagram of another embodiment of the arrangement according to the present invention.

There are several ways to use the MPI system as MRI system. In a first embodiment as illustrated in FIG. 7 shimming coils 83 (and a corresponding shimming coil signal generator unit 80 including a current source 81 and a filter 82) are added to generate a low field strength magnetic field with sufficient homogeneity for MRI operation. Further, an RF sender 63, in particular an RF transmit coil 63, is added coupled to a transmit signal generator unit 60 (including a send amplifier 61 and a filter 62) to generate the necessary RF field for excitation. The system may operate at about 50 mT.

In a second embodiment, as shown in FIG. 6, the transmit signal generator unit 60 is coupled to the receiver means 54, i.e. the receive coil, for generating the necessary RF field.

In a third embodiment only the shimming coils 83 and the shimming coil signal generator unit 80 are added (but no transmit signal generator unit 60 and RF sender 63). Hence, there is no RF $B_1$ field at the receive frequency available. The RF pulse is generated by cycling the main field down to a level, where the drive field frequency is the Larmor frequency. Receiving is thereafter done after ramping to e.g. 50 mT. Alternatively, the RF pulse is generated by decreasing the main magnetic field down to zero field and increasing the main field thereafter using a different magnetization direction. In particular, the main magnetic field is generated again in a direction, which does not correspond to the present magnetization direction, which generally corresponds to the direction of the main magnetic field that had existed shortly before reaching zero value when decreasing the main magnetic field.

In a fourth embodiment neither any shimming coils 83 (and shimming coil signal generator unit 80) nor any transmit signal generator unit 60 and RF sender 63 are added. A trivial solution for a homogeneous field is the zero field. At zero field, the spins remain their initial orientation. If now a homogeneous field is added, pointing to a different direction, the magnetization will start to perform a precession movement. Hence, an RF pulse was applied. For recording, the main field is ramped to a value, where the MPI recording system is efficient.

This type of MPI needs some sort of adaption of the sequences. For example, a spin echo is only a reversal of the magnetic field direction. For a volume selection, a field free point (FFP) is moved from infinity to the center of the desired field of view while maintaining a strong gradient. Then the gradient is reduced to zero and the RF sequence is applied.

There are features in the proposed MPI/MRI combination, which are not possible with classical MRI. For example, the magnetization direction can be turned to a direction where the recording system is most efficient. It is also possible, to bend the $B_0$ field while recording. This gives more freedom in parallel imaging, as there are three magnetization directions available, in particular for sensitivity encoding (also referred to as SENSE in conventional MRI, described e.g. in K. P. Pruessmann, et al., Sensitivity encoding for fast MRI: SENSE, MAGMA 6(1):87, 1998).

The possibility to change the main field strength allows the use of contrasts depending on the $B_0$ dependent T1 e.g. for nitrogen imaging. The scanner is inherently a multi-nuclei system allowing for imaging of hyperpolarized noble gases. Paramagnetic implants have a minor effect on the image quality and scanning is done with minimal heating of implants. So some patients can be scanned with this scanner, who are not allowed to conventional MRI systems. Especially, it is possible to look inside of stents.

The arbitrary orientation of the $B_0$ field allows other contrasts, like the unambiguous determination of the tissue electrical conductivity. As $B_0$ can be low, the conductivity can be imaged for frequencies below 1 MHz, where the tissue variation best reflects pathologies. Moreover frequency dependent conductivities can be recorded.

Before discussing further specific applications, scenarios for the provision of an "anatomical reference" shall be discussed. MPI images the distribution of magnetic particles. To interpret these data, it is helpful to refer to an image of the underlying anatomy. There are may ways to get this information. The simplest is to register images of other modalities to MPI images using markers that can be identified in both modalities. It is also possible to place a CT system next to an MPI scanner. When using the same patient support for both modalities (called "shared table"), registration of the images becomes simple. Nevertheless, some sort of fusion is still necessary, possibly leading to uncertainties in the fused images. Also, the additional imaging system implies higher cost and more effort in patient handling.

Therefore, an intrinsic combination of MPI with an anatomical reference image seems to be useful. One such combination would be with magnetic resonance imaging which seems to be technically feasible. Both MPI and MRI use strong magnetic fields and record weak oscillating fields. The field geometries and frequencies are not identical, but with moderate technical effort components may be designed serving both MPI and MRI. For example, if the selection field in MPI is generated by electromagnets, a reverse current in one coil yields a homogeneous field suitable for polarizing the protons. The field strength for MRI may reach 0.5 T for resistive coils and 1 T or more for superconducting coils.

There are a variety of effects that make an intrinsic MPI/MRI combination problematic. For MRI, the fields need to be very homogeneous but simply changing the current direction in one coil usually does not provide a field with sufficient homogeneity because such a coil assembly would be not very efficient for selection field generation. The MPI system contains no sender for the RF $B_1$ field and no recording system for frequencies as high as several ten MHz. Moreover, the MPI drive and recording coils have self-resonances in the low MHz range making the addition of a MRI $B_1$ coils difficult.

One solution for these technical challenges would be to construct a field cycling or pre-polarized MRI system as described by Macovski A, Conolly S, "Novel approaches to low-cost MRI", Magn. Reson. Med. 1993 Aug. 30, (2):221-30. In such a system a strong, but not necessarily very homogeneous field is applied for several hundreds of milliseconds to polarize the protons. After the polarizing pulse the field is reduced to a much lower value where the RF pulses are applied. In MRI, the field homogeneity needs to be roughly 10 $\mu T \mu_0^{-1}$ which is 10 ppm for a 1 T scanner but 1% for a 1 mT scanner. Such a value could be reached by changing the current direction in the selection field coils.

Going to such a low field, the RF pulses can be applied using the drive field coil. The Larmor frequency of protons at 0.6 mT is 25 kHz, i.e. the currently used MPI drive field frequency. The drive field amplitudes in an MPI scanner exceed the necessary amplitudes for MRI by far. An alternative to the drive field for the RF pulse is the focus field. It contains frequency components of up to about 1 kHz. Therefore, the $B_0$ field has to be even lower, when applying the RF pulse. The focus field amplitude is so high, that the RF pulse may be described as:
  i) Polarize the protons using a strong $B_0$ field (using the selection field coils, and eventually part of the focus field coils and/or—if available—extra shimming coils).
  ii) Reduce the field strength to zero.
  iii) Increase the field value using a direction which is not identical with the proton polarization (this is the "RF pulse" i.e. the cause of precession). The magnetization direction is preferably rotated for instance by 90°.
  iv) Ramp the field up to achieve a convenient Larmor frequency for signal recording (e.g. 1 MHz).

A spin echo using this method would be a simple field reversal.

A pre-polarized MRI would certainly be sufficient for the anatomical reference in MPI. For some selected applications, it may be even superior to the traditional way of MRI. For patients with implants, a pre-polarized MRI would allow near implant imaging as long as the implant is not ferromagnetic. The MPI/MRI combination would be able to operate at even lower frequencies; therefore it would be possible to image inside of metallic stents, possibly assessing re-stenosis. The field cycling allows contrasts, not accessible by conventional MRI. For example, the protein content of tissue can be imaged using the field dependent $T_1$ relaxation times.

Advantageously, a MPI and a MRI signal acquisitions can be done in a combined MPI/MRI mode. In particular, while acquiring MPI detection signals at one location in the region of action, the protons can be polarized at other locations (e.g. with a field intensity of up to 0.2 T). The step of polarization is the time-critical step of pre-polarized MRI. Hence, e.g. approximately 10% of the measurement time of MPI can be used for MRI, but nevertheless a MR image having the same quality as a MR image obtained with data acquired during 100% of the time usually required for MRI data acquisition can be obtained. It could also be useful to measure the MR signal at the same location where the MPI signals are obtained since the polarization of the protons will be transported to this location by the blood flow, which enables to obtain a perfusion image.

As the focus field of an MPI system can point in any direction, a pre-polarized MPI/MRI combination has the ability to direct $B_0$ arbitrarily. This allows an efficient utilization of the recording coils. Moreover it could solve the problem of current mapping using MRI for electrical impedance measurement in anisotropic tissue. In conventional MRI, only one field component can be measured in the case of low frequency current density imaging. There a phase shift is generated by applying a current through the patient at low frequencies. This is only sensitive to the field component on $B_0$-direction. Therefore it is impossible to reconstruct the full current densities. With high frequency current density imaging, two field components can be detected. In this technique, fields due to the currents act as MRI RF fields. Usually, eddy currents in the patient due to $B_1$ field is utilized. Still, a full reconstruction of the current density is impossible.

With the proposed prepolarized MPI/MRI combination, all field components can be measured. This allows to reconstruct the anisotropy of the tissue conductivity. Moreover, the ability to choose the Larmor-frequency allows to use current injection frequencies, where minimal effect on the patient is expected but still strong tissue specific contrast is anticipated i.e. at around 100 kHz.

As such an MPI/MRI system has the ability to rapidly change the field strength and as it is equipped with a very broad-banded receiving system, is may also be well suited for multi-nuclei MRI. As other nuclei than protons produce relatively weak signal, the presumably low $B_0$ field strength of an MPI/MRI system is not ideal. On the other hand, there are hyperpolarized techniques in MRI using xenon $^{129}Xe$ and helium $^3He$ for lung imaging and carbon $^{13}C$ for metabolic imaging. Finally, proton lung images with improved quality could be expected, as the susceptibility artefacts are much less severe at low read-out field strength.

In summary, magnetic particle imaging allows the imaging of fast tracer dynamics, but there is no native tissue contrast. A combination with MRI solves this issue. However, coil geometries in MPI and MRI differ significantly, making direct use impractical. According to one aspect of the present invention it is proposed to use pre-polarized MRI to overcome these difficulties. Further, methods and arrangements are proposed to achieve MRI imaging with minimal additional hardware.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:
1. An arrangement for influencing and/or detecting magnetic particles in a region of action and for magnetic imaging of an examination object in said region of action, which arrangement comprises:
  a set of coils,
    wherein, in a magnetic particle imaging mode, the set of coils are operable to generate
      a stationary magnetic gradient field having a pattern in space of a magnetic field strength such that a first sub-zone having a low magnetic field strength and a second sub-zone having a higher magnetic field strength are formed in the region of action,
      a temporally changing homogeneous magnetic field for changing the position in space of the region of action and for changing the position in space of the two sub-zones in the region of action so that a magnetization of the magnetic material changes locally, and
    wherein, in a magnetic resonance imaging mode, the set of coils are operable to generate
      a substantially homogeneous main magnetic field in a selected and changeable direction, and
      a magnetic gradient field in at least two selected and changeable directions;

an excitation means configured to excite magnetic spins in the region of action to precess;

a receiving means configured to selectively acquire magnetic resonance signals and detection signals depending on the magnetization in the region of action, which magnetization is influenced by the change in the position in space of the first and second sub-zone;

signal generation means configured to generate and provide field generation signals to said set of coils;

control means configured to control said signal generation means; and processing means configured to process said detection signals and said magnetic resonance signals.

2. An arrangement as claimed in claim 1, wherein said set of coils includes:

a first subset of coils for generating said magnetic gradient field;

a second subset of coils for generating said temporally changing homogeneous magnetic field for changing the position in space of the region of action; and a third subset of coils for generating said temporally changing homogeneous magnetic field for changing the position in space of the two sub-zones in the region of action so that the magnetization of the magnetic material changes locally.

3. An arrangement as claimed in claim 2, wherein said substantially homogeneous main magnetic field in a selected and changeable direction is generated by said first and/or second subset of coils, and wherein said magnetic gradient field in at least two selected and changeable directions is generated by said second subset of coils.

4. An arrangement as claimed in claim 2, wherein said first subset of coils includes selection field coils for generating a magnetic selection field as said magnetic gradient field, wherein said second subset of coils includes focus field coils for generating a magnetic focus field as said temporally changing homogeneous magnetic field for changing the position in space of the region of action, and wherein said third subset of coils includes drive field coils for generating a magnetic drive field as said temporally changing homogeneous magnetic field for changing the position in space of the two sub-zones in the region of action so that the magnetization of the magnetic material changes locally.

5. An arrangement as claimed in claim 2, wherein said first subset of coils comprise a number of at least two of first coil elements located on opposite sides of the region of action, each first coil element being provided with a separate first field generation signal from said signal generation means.

6. An arrangement as claimed in claim 2, wherein said second subset of coils includes a number of at least six of second coil elements located on opposite sides of the region of action, each coil element being provided with a separate second field generation signal from said signal generation means.

7. An arrangement as claimed in claim 2, wherein said third subset of coils is adapted for generating RF transmit signals in a magnetic resonance imaging mode.

8. An arrangement as claimed in claim 1, wherein said control means is further adapted for controlling said signal generation means to generate and provide field generation signals to said set of coils to generate a magnetic field having bent magnetic field lines.

9. An arrangement as claimed in claim 1, wherein said control means is adapted to switch between the magnetic particle imaging mode and the magnetic resonance imaging mode and to control said signal generation means for generating and providing field generation signals to said set of coils as required in the respective mode.

10. An arrangement as claimed in claim 1, further comprising shimming coils for generating a substantially homogeneous main magnetic field in a magnetic resonance imaging mode.

11. An arrangement as claimed in claim 1, wherein said excitation means includes an RF transmit coil and/or an RF signal generator coupled to said receiving means for generating RF transmit signals in a magnetic resonance imaging mode.

12. An arrangement as claimed in claim 1, wherein said control means is adapted for controlling said signal generation means to generate and provide field generation signals to said set of coils to subsequently generate in the region of action a magnetic gradient field, a first substantially homogenous magnetic field in a first magnetization direction, and after reducing a field intensity of the first substantially homogenous magnetic field, a substantially homogenous magnetic field in a second magnetization direction which is substantially different from the first magnetization direction.

13. An arrangement as claimed in claim 1, wherein said control means is further adapted for controlling said signal generation means to generate and provide field generation signals to said set of coils to subsequently generate a strong magnetic gradient field, reduce the gradient of said magnetic gradient field and add a substantially homogeneous magnetic field, and reduce the field strength of said magnetic gradient field, and wherein magnetic resonance signals are then acquired.

14. An arrangement as claimed in claim 1, wherein said control means is further adapted for controlling said signal generation means to generate and provide field generation signals to said set of coils for pre-polarizing protons at portions of the region of action for subsequent acquisition of magnetic resonance signals from said portions, while detection signals are acquired from other portions of said region of action.

15. A non-transitory computer program comprising program code means for causing a computer to control an arrangement as claimed in claim 1.

16. A method for influencing and/or detecting magnetic particles in a region of action and for magnetic resonance imaging of an examination object in said region of action, which method comprises the steps of:

generating, in a magnetic particle imaging mode, a stationary magnetic gradient field having a pattern in space of a magnetic field strength such that a first sub-zone having a low magnetic field strength and a second sub-zone having a higher magnetic field strength are formed in the region of action, a temporally changing homogeneous magnetic field for changing a position in space of the region of action and a temporally changing homogeneous magnetic field for changing a position in space of the two sub-zones in the region of action so that the magnetization of the magnetic material changes locally;

generating, in a magnetic resonance imaging mode, a substantially homogeneous main magnetic field in a selected and changeable direction, and a magnetic gradient field in at least two selected and changeable directions;

in the magnetic resonance imaging mode, exciting magnetic spins in the region of action to precess;

selectively acquiring magnetic resonance signals in the magnetic particle imaging mode and detection signals depending on the magnetization in the region of action in the magnetic resonance imaging mode, which magnetization is influenced by the change in the position in space of the first and second sub-zone; and processing said detection signals and said magnetic resonance signals.

17. A method as claimed in claim 16 further comprising:
the steps of subsequently generating in the region of action
a magnetic gradient field,
a first substantially homogenous magnetic field in a first magnetization direction, and
after reducing a field intensity of the first substantially homogenous magnetic field, a substantially homogenous magnetic field in a second magnetization direction which is substantially different from the first magnetization direction.

\* \* \* \* \*